United States Patent [19]
Myers et al.

[11] Patent Number: 5,999,257
[45] Date of Patent: Dec. 7, 1999

[54] METHOD AND APPARATUS FOR MONITORING PARTICULATES USING BACK-SCATTERED LASER WITH STEERABLE DETECTION OPTICS

[75] Inventors: Richard Myers, Gibsonia; Edward A. Smierciak, Pittsburgh, both of Pa.

[73] Assignee: United Sciences, Inc., Gibsonia, Pa.

[21] Appl. No.: 09/002,984

[22] Filed: Jan. 5, 1998

Related U.S. Application Data

[63] Continuation-in-part of application No. 08/856,072, May 14, 1997, Pat. No. 5,831,730, which is a continuation-in-part of application No. 08/761,127, Dec. 6, 1996, Pat. No. 5,751,423.

[51] Int. Cl.[6] .................................................. G01N 15/02
[52] U.S. Cl. ........................ 356/336; 356/339; 356/343
[58] Field of Search .................................. 356/336, 339, 356/343

[56] References Cited

U.S. PATENT DOCUMENTS

| | | | |
|---|---|---|---|
| 3,526,460 | 9/1970 | Webb | 356/36 |
| 3,797,937 | 3/1974 | Shoffner | 356/102 |
| 3,915,572 | 10/1975 | Orloff | 356/106 R |
| 4,017,186 | 4/1977 | Shoffner et al. | 356/103 |
| 4,221,485 | 9/1980 | Schulze | 356/338 |
| 4,541,719 | 9/1985 | Wyatt | 356/343 |
| 4,577,964 | 3/1986 | Hansen, Jr. | 356/39 |
| 4,791,427 | 12/1988 | Raber et al. | 343/754 |
| 5,132,548 | 7/1992 | Borden et al. | 250/574 |
| 5,173,958 | 12/1992 | Folsom et al. | 385/36 |
| 5,471,299 | 11/1995 | Kaye et al. | 356/356 |
| 5,565,984 | 10/1996 | Girvin | 356/336 |
| 5,767,967 | 6/1998 | Yufa | 356/336 |

OTHER PUBLICATIONS

Catalogue of Durag Industrie Elektronik entitled D–R–300 dated Jan., 1993.

Catalogue of Durag Industrie Elektronik entitled Line of Products dated Jan., 1993.

Catalogue of Enviromental Systems Corporation entitled Particulate Monitor Model P–5A, undated.

Sick Optic Electronic Operating, Maintenance and Service Manual GM 30/$SO_2$/$NO_2$/Opacity Combined Analyzer. Description and Operation, Cover, pp. 34, 38–41, 44–48, Apr., 1988.

Esko Dust/Opacity Monitor Brochure, MIP Laser/Dust Opacity Monitor For Emission Monitoring And Process Contro.

Insitec Measurement Systems Brochure.

Particle Measurement Systems, Inc., brochure Aerosol Multiplexing Manifold System Model Am–12, Mar., 1985.

TSI Particle Instruments Brochure entitled "New Ideas In," 1994.

Particle Measurement Systems, Inc., Operating Manual for Model 300 Series Continuous Aerosol Monitoring System, Revision 7, Jan., 1989.

*Primary Examiner*—Robert H. Kim
*Assistant Examiner*—Reginald A. Ratliff
*Attorney, Agent, or Firm*—Buchanan Ingersoll, P.C.

[57] ABSTRACT

In a method for monitoring particulates in stacks or ducts a back-scatter monitor uses a solid-state laser to emit a collimated beam, the intensity of which is controlled via feedback from a reference detector. The beam is split so that part goes to a reference surface for calibration checks, and part is directed to pass at a selected angle through a gaseous sample. Optical energy scattered from particles in the sample is detected by viewing optics to provide an indication of particulate concentration. The beam steering mechanism can direct the optics to view scattering along a selectable axis that intersects the laser beam at a specified location within the gaseous sample. The method can be used to determine the opacity of the gaseous sample providing a basis for correlation to particulate loading of that portion of the particulates that are of a size comparable to the wavelength of light.

17 Claims, 7 Drawing Sheets

METHOD AND APPARATUS FOR MONITORING PARTICULATES USING BACK-SCATTERED LASER WITH STEERABLE DETECTION OPTICS

CROSS REFERENCE TO RELATED APPLICATION

This is a continuation in part of United States patent application Ser. No. 08/856,072, filed May 14, 1997, now U.S. Pat. No. 5,831,730 which is a continuation in part of United States patent application Ser. No. 08/761,127, filed Dec. 6, 1996, now U.S. Pat. No. 5,751,423.

FIELD OF INVENTION

This invention generally relates to back-scattering particulate monitors of the type wherein the empirically determined particulate concentration is correlated to the measurement of light back-scattered from a beam of light. Such devices are used for monitoring particulate concentration within stacks or ducts which contain the gases resulting from the burning of fossil fuel or incineration of waste materials, or process gases which contain particulates from industrial processes.

DESCRIPTION OF THE PRIOR ART

Various government and environmental agencies have set limits as to the amount of particulates and other pollutants that an electric utility or other industry may emit into the air. Typically particulate emissions are determined from measurements of the stack gasses as they flow through the stack or connecting ductwork. Back-scatter monitors have been used as correlation devices to monitor the mass concentration of dust and other particulates passing through a stack or other conduit. The measurement of optical back-scattering or reflection is compared to the results obtained by drawing an isokinetic sample from the process, with particulate concentration determined via weighing of a filter through which a known quantity of sample was passed, and a correlation coefficient is determined, which establishes the relationship between the optical measurement and the particulate concentration.

ESC, Durag and Irwin Sick manufacture instruments that essentially measure the energy that is scattered at angles ranging from 90° to 160° with respect to the original propagated direction of the beam. United Sciences manufactures an instrument that measures directly (178° to 180°) back-scattered light.

A disadvantage common to the prior art involves the issue of calibration checks. The United States Environmental Protection Agency (EPA), as well as the European TUV, requires that a monitor that is being used to demonstrate compliance with particulate emission standards be equipped with a mechanism that can be used to simulate a condition of zero particulate, and a condition equivalent to a predetermined upscale particulate concentration. These must be performed, at a minimum, once every 24 hours. Even when the particulate monitor is not being used for regulatory compliance, the user prefers to have this feature as a part of the system. The prior art in back-scattering monitors typically achieves the zero condition by establishing a direct optical path between the source and the detector via such means as reorienting the source and detector or inserting a mirror or fiber optic cable, while simultaneously blocking the optical path across the stack. Optical filters are used to match the optical energy in the simulated zero path to the optical energy when viewing a clear stack path. An upscale condition is simulated by interposing an additional optical filter into that optical path. In the prior art, implementation of this calibration check typically requires the use of additional mechanical moving parts such as solenoids, motors, bearings, and electrical relays.

A related disadvantage of the prior method of performing a zero and upscale calibration check is that, when the instrument is re-calibrated for a different particulate concentration, the gain factors of the instrument need to be adjusted. In prior designs, this would require manually changing optical filters in the instrument. In most instances, nothing is done to match the optical energy in the zero check mode to the optical energy in the clear-stack condition. Instead, the energy mismatch is accounted for in software, which results in less-than-ideal zero and span check because the detector is being evaluated at different operating points than are used for the actual measurement. Because all instruments of this type are effectively calibrated after installation on the stack and performance of isokinetic sampling to determine the correlation factors, this means that most or all back-scatter instruments, once installed, do not have span and zero checks that actually simulate the equivalent stack measurements in terms of optical energy reaching the detector.

A final disadvantage of the prior designs lies in the fact that the measurements is made near the wall of the stack. All prior designs project the beam of light into the stack at a fixed angle and view the back-scattered energy at a second fixed angle, thereby defining a scattering volume at a fixed distance from the stack wall. None of these designs present a non-manual way to change the location of the scattering volume or to be able to measure the spatial profile of particulate within the stack.

There thereby exists a need for a back-scatter particulate monitor that can perform simulated calibration zero and span checks that can be automatically adjusted so as to correctly simulate equivalent stack measurements whenever the full scale concentration of the instrument is changed, without the need for additional moving parts. The instrument should also possess the capability to measure the back-scattered energy from selected locations within the stack so as to provide data regarding the profile of particulate distribution within the stack.

SUMMARY OF THE INVENTION

We provide a back-scattering monitor which preferably contains a solid state laser light source which requires low power, is light and rugged, gives off low heat, has long life and can be directly modulated. One could use an LED as the solid state light source. The light source is collimated into a narrow axial beam and is projected into the stack at an angle such that it crosses the center axis of the optical system at a known distance from the stack wall. The viewing optics, which receives and measures back-scattered energy from particles within the stack, is dynamically steered so as to view scattering from a selectable scattering volume within the stack.

One embodiment of our monitor steers the viewing optics using rotating cylindrical prisms. Normally, the control of viewing optics using these devices is complex because the effect of moving one prism is dependent on the current position of the other prism. However, by tilting the optical assembly, it is possible to create an optical configuration in which independent movement of either prism results in movement of the beam in mutually orthogonal directions. This permits use of a simple control algorithm.

We further prefer to provide that, in addition to the ability to point the viewing optics at different scattering locations within the stack, the mechanism is able to direct the beam in any other desired direction, in a way that simplifies the zero and upscale calibration checks. Rather than mechanically moving the source and detector assemblies and interposing optical filters into the beam path, our system directs the viewing optics onto pre-calibrated surfaces of known illumination and reflectivity. Thus, no additional moving parts are required other than those already used to steer the viewing optics. Furthermore, each calibration target is shaped such that, by moving the steered viewing optics slightly, the portion of the illuminated calibration target that is viewed can be adjusted, thereby making possible an exact match between the optical energy viewed in the calibration mode and the optical energy corresponding to any desired fraction of any desired full scale of measurement of particulate in the stack measurement mode.

Our monitor is useful for measuring particulate concentration and its spatial distribution within stacks or ducts, with automatic energy-matching of span and zero checks, features which prior back-scattering instruments do not possess. Our device can be used to measure corrosive, hot, vibration-prone environments within large utility and industrial stacks and ductwork.

Other objects and advantages of our monitor will become apparent from a description of certain present preferred embodiments shown in the drawings.

DESCRIPTION OF THE PREFERRED EMBODIMENTS

Figure 1:
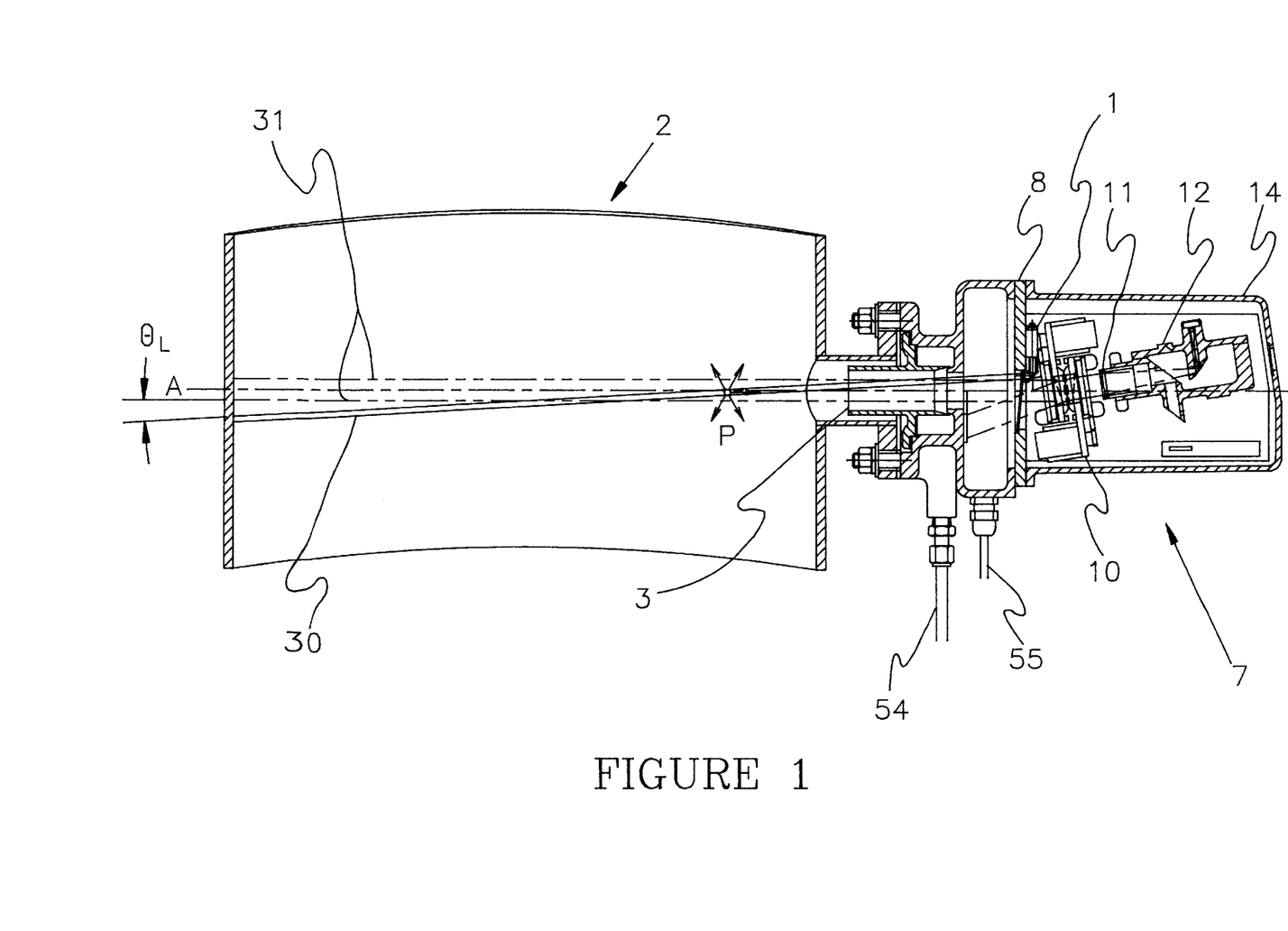
FIG. 1 is a side view partially in section of a present preferred embodiment of our monitor mounted on a portion of a stack or duct.

Referring to FIG. 1, our system has an optical assembly or main assembly 7 which is mounted onto a conduit 2. This conduit may be a stack or duct containing the gases resulting from burning fossil fuel, or process gases which contain particulates from industrial processes such as, but not limited to waste incineration, lime kilns, petrochemical processes, food processing, and measurement of dust in mine shafts or vehicular tunnels. The conduit 2 illustrated in the drawings is shown to be quite small. This was done only for illustrative purposes as we expect our monitor to be used in conduits ranging in size from a less than a meter to over 20 meters in diameter.

A collimated beam of light 30 is projected from a solid state light source 1 in assembly 7, into the conduit 2 in which the particulate is to be measured. We prefer to use a laser as the solid state light source, but a light emitting diode could be used. As is depicted in FIG. 1, the light beam 30 is projected at an angle $\Phi_L$ with respect to an axis of symmetry of the system A—A shown in FIGS. 1 and 2. Consequently, the laser beam is beneath the field of view 31 of the viewing optics prior to arrival at the opposite wall of conduit 2 with the desirable result that reflected light from the opposite wall does not create a false indication of light scattering from particulates.

Figure 2:
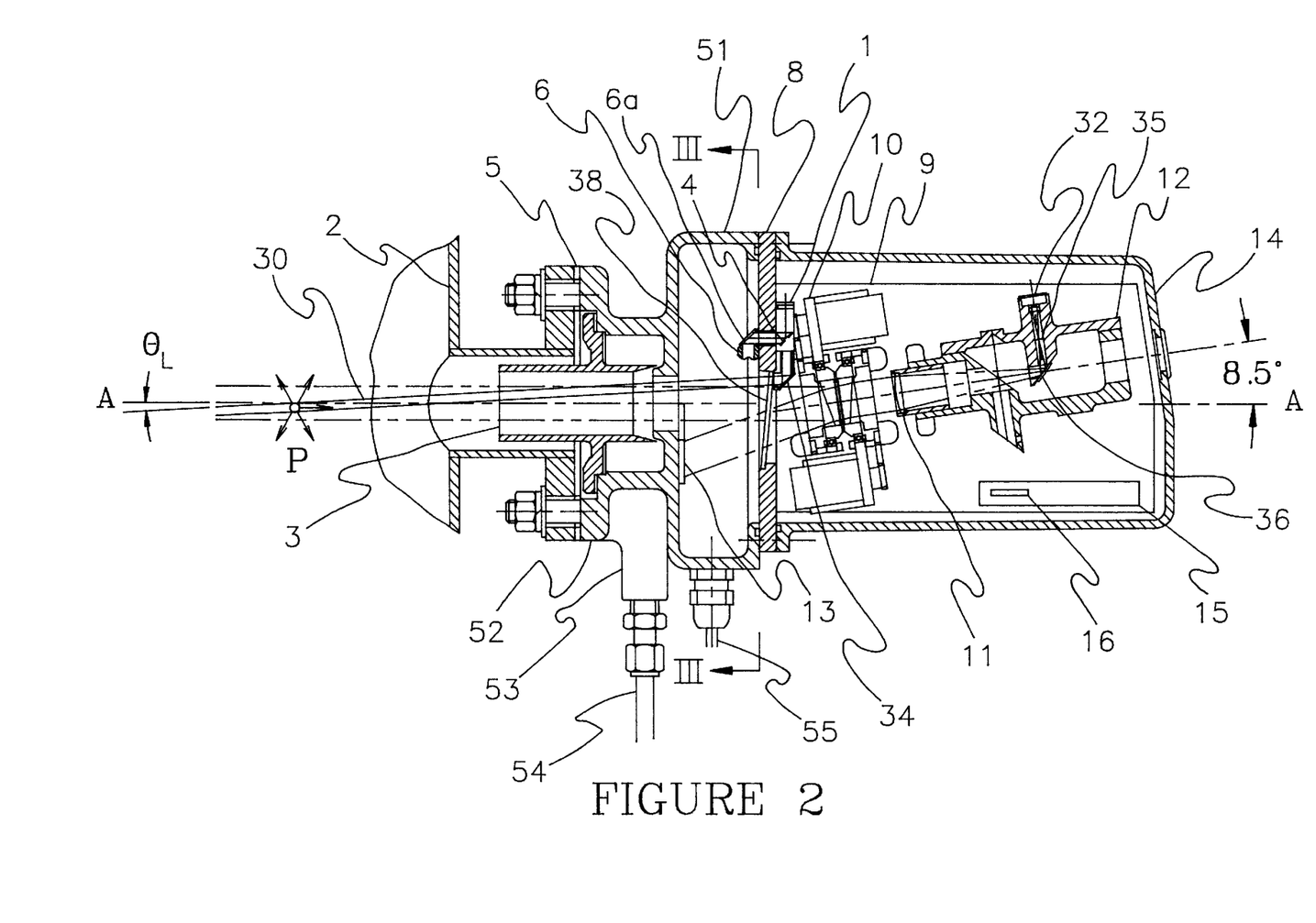
FIG. 2 is a side view partially in section of the optical assembly of the embodiment of FIG. 1.

FIG. 2 shows the main assembly 7 in more detail. A light beam indicated in solid line from solid state laser module 1 is reflected off mirror 34 from whence the beam traverses the stack 2. Back-scattered light from particulate P passes through the view-steering apparatus 10, the beam converger 11 to mirror 36 which reflects the beam through field stop 35 to signal detector 32. If desired an aperture may also be used to restrict the optical path.

The solid state laser module 1 contains an internal reference detector (not shown), the output of which is used to enable the power to laser 1 to be controlled so as to maintain a constant laser intensity.

Figure 3:
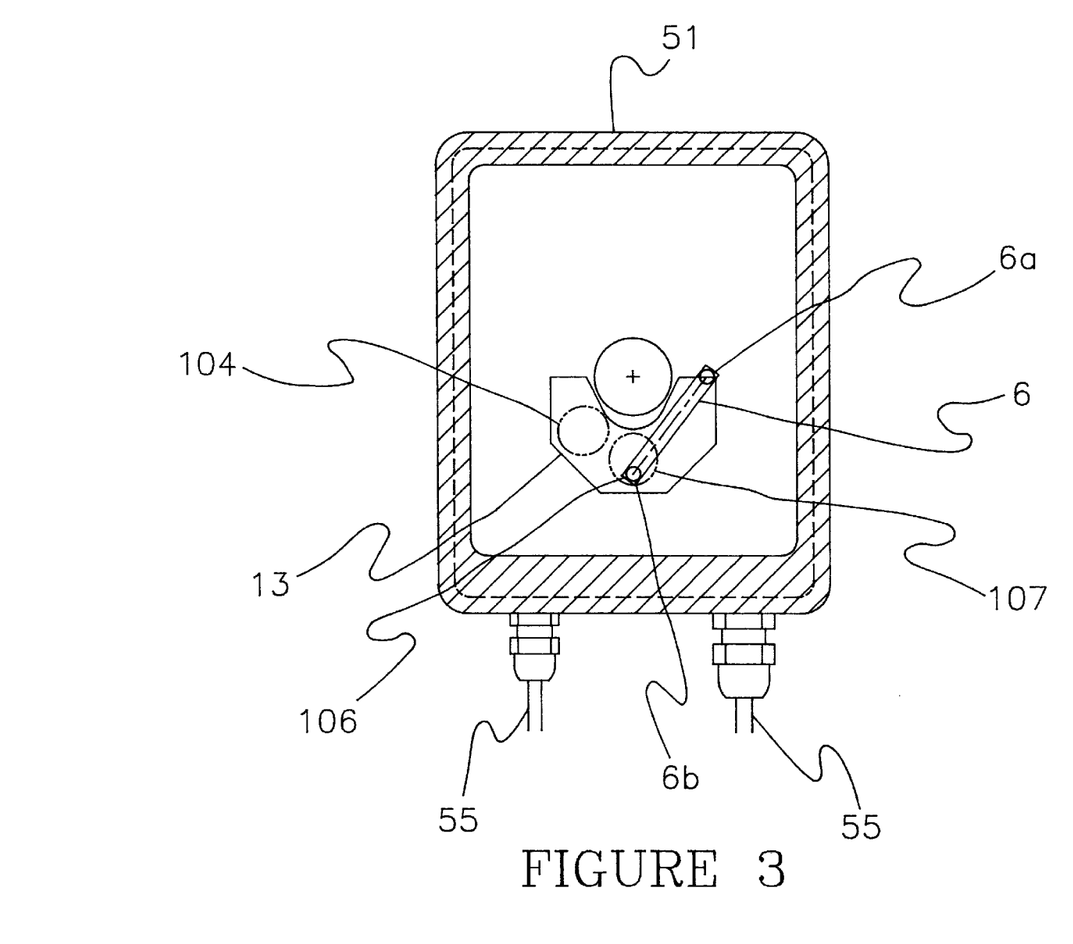
FIG. 3 is a sectional view taken along the line III—III of FIG. 2.

Light emitting from the laser 1, prior to arriving at mirror 34 is made to traverse a beam splitter 4, which allows most of the light, typically 90%, to pass through to mirror 34, while the remaining 10% is reflected into a set of relay optics 6 which directs the reflected light to a calibration fixture 13 inside the intermediate housing 51 as shown in FIG. 3. The use of the calibration fixture will be discussed in more detail in a later section.

Figure 4:
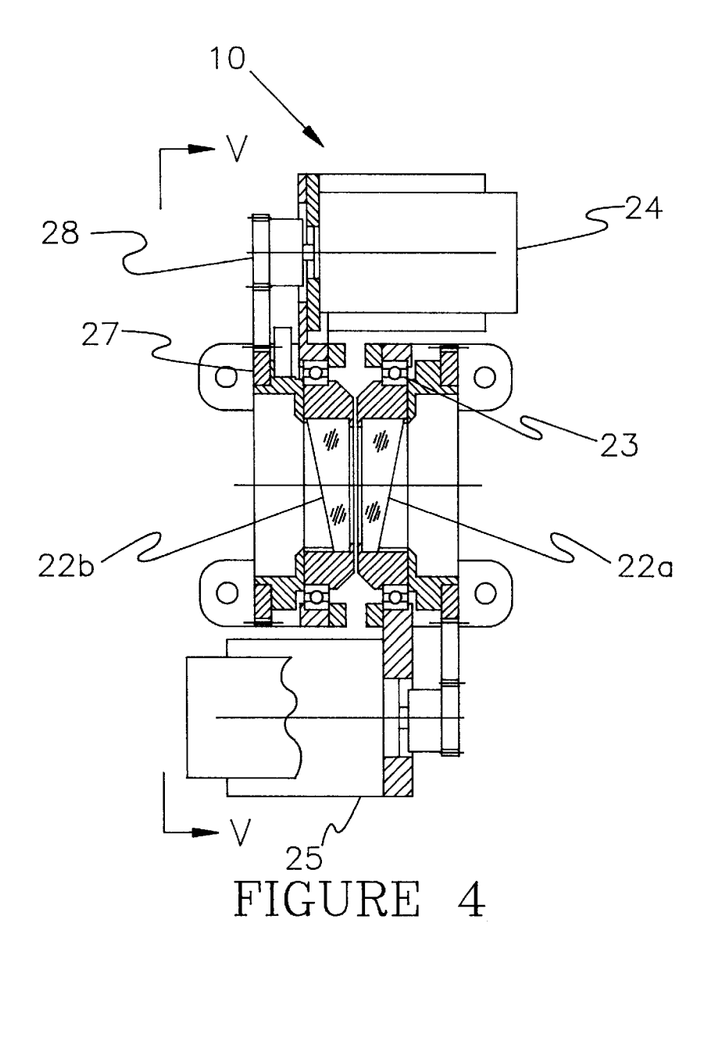
FIG. 4 is a side view partially in section of the view steering mechanism of the embodiment of FIG. 1.
Figure 5:
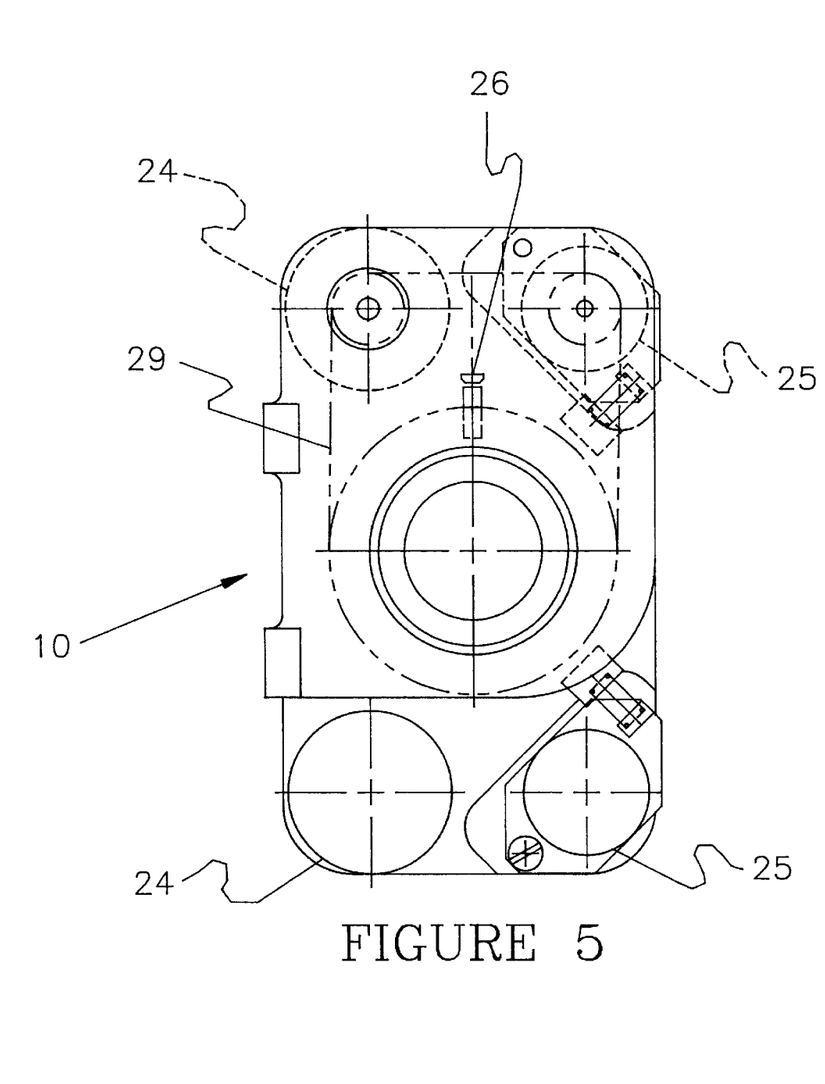
FIG. 5 is an end view of the view steering mechanism of FIG. 4 taken along the line V—V.

As illustrated in FIGS. 4 and 5, the preferred view-steering apparatus 10 consists of two similar assemblies, each containing one of two wedge prisms 22a and 22b. Each prism is axially aligned with beam converger 11 shown in FIG. 2. As can be seen is FIG. 5, there is a servo motor 24, timing belt 29 and encoder 25 associated with each prism. Each prism can be independently rotated via bearings 23, timing belt 29 driven by servo motor 24 and encoder 25. Each prism is associated with a homing switch 26 which is used as a reference point for the encoder 25. Homing switch 26 is activated once per revolution of the associated prism 22a or 22b. Each encoder is related to a prism via a 4:1 gear ratio such that the encoder rotates 4 times per prism rotation. Each encoder 25 has three square-wave outputs: (1) a once-per-encoder pulse, (2) a 0°-phase pulse for each 0.18 degrees of rotation of the encoder, and (3) a 90°-phase pulse, that lags the 0°-phase pulse by a quarter-cycle, for each 0.18 degrees of rotation of the encoder. The 0° and 90° phase pulses indicate which direction the encoder is turning. The encoder resolution, combined with the 4:1 gear ratio, enables the system to know the rotation of the prisms by ±0.045°.

We prefer to use wedge prisms which are able to cause a deflection of 6° in the direction of the beam passing through it. Rotating either prism about 360° causes the expanded laser beam to describe a circle corresponding to a 6° deflection of the beam. By independently controlling the motion of the two prisms, the beam can be steered to any direction inside a 12° deviation from its original direction. Since the system can identify prism rotation to within ±0.045°, and since a 180° prism rotation creates a change of direction of 6° in the transmitted beam, it follows that we are able to identify the beam direction to within ±(0.045/180) (6°)=±0.0015°. At a distance of 2 meters, this corresponds to a beam deflection of (200 cm)tan (±0.0015°)=±0.05 mm. This is more than adequate resolution for pointing the view-steering optics to any desired location within the stack.

Figure 6:
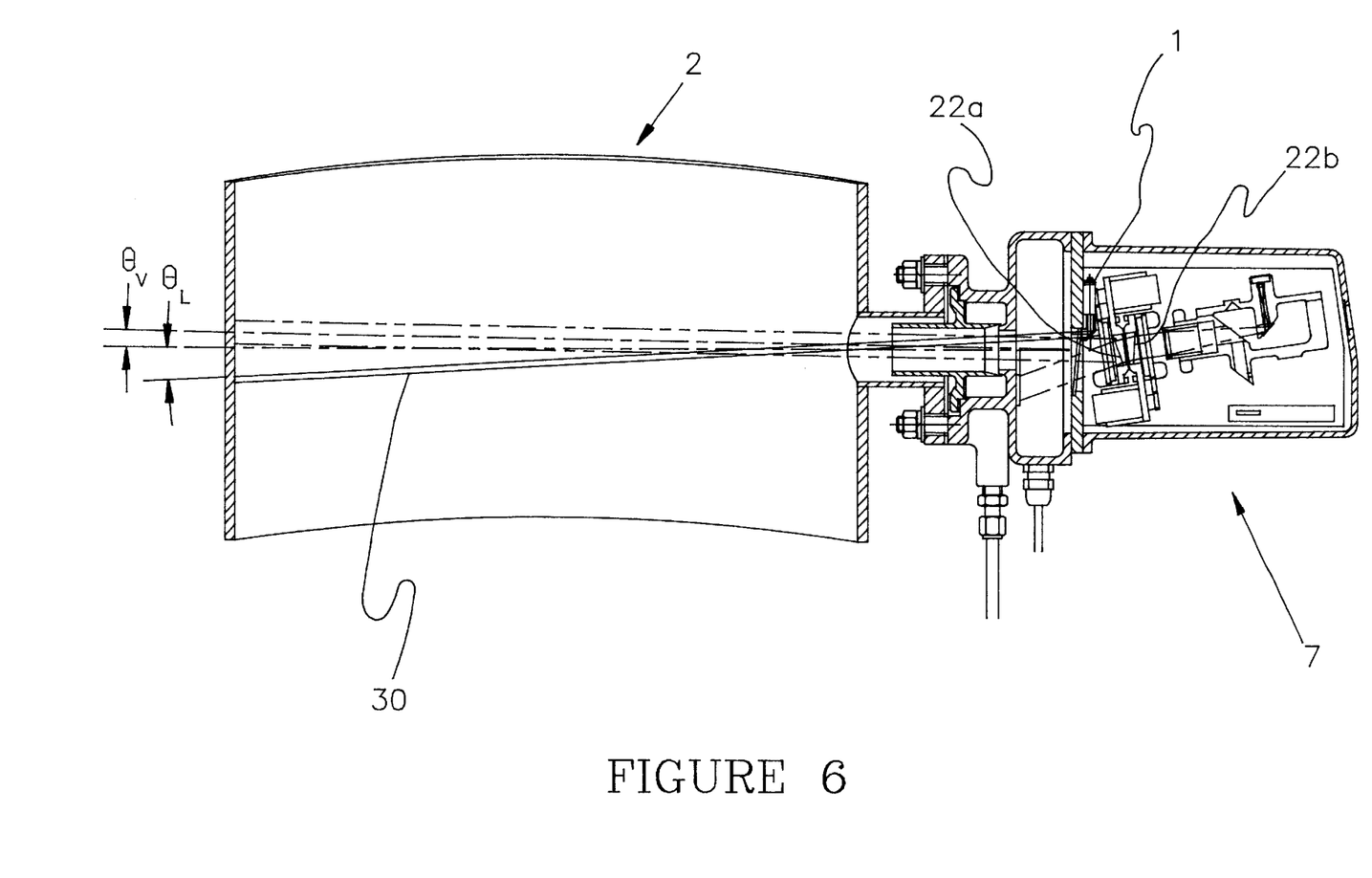
FIG. 6 is an optical diagram showing the light path when the viewing optics are steered high.
Figure 7:
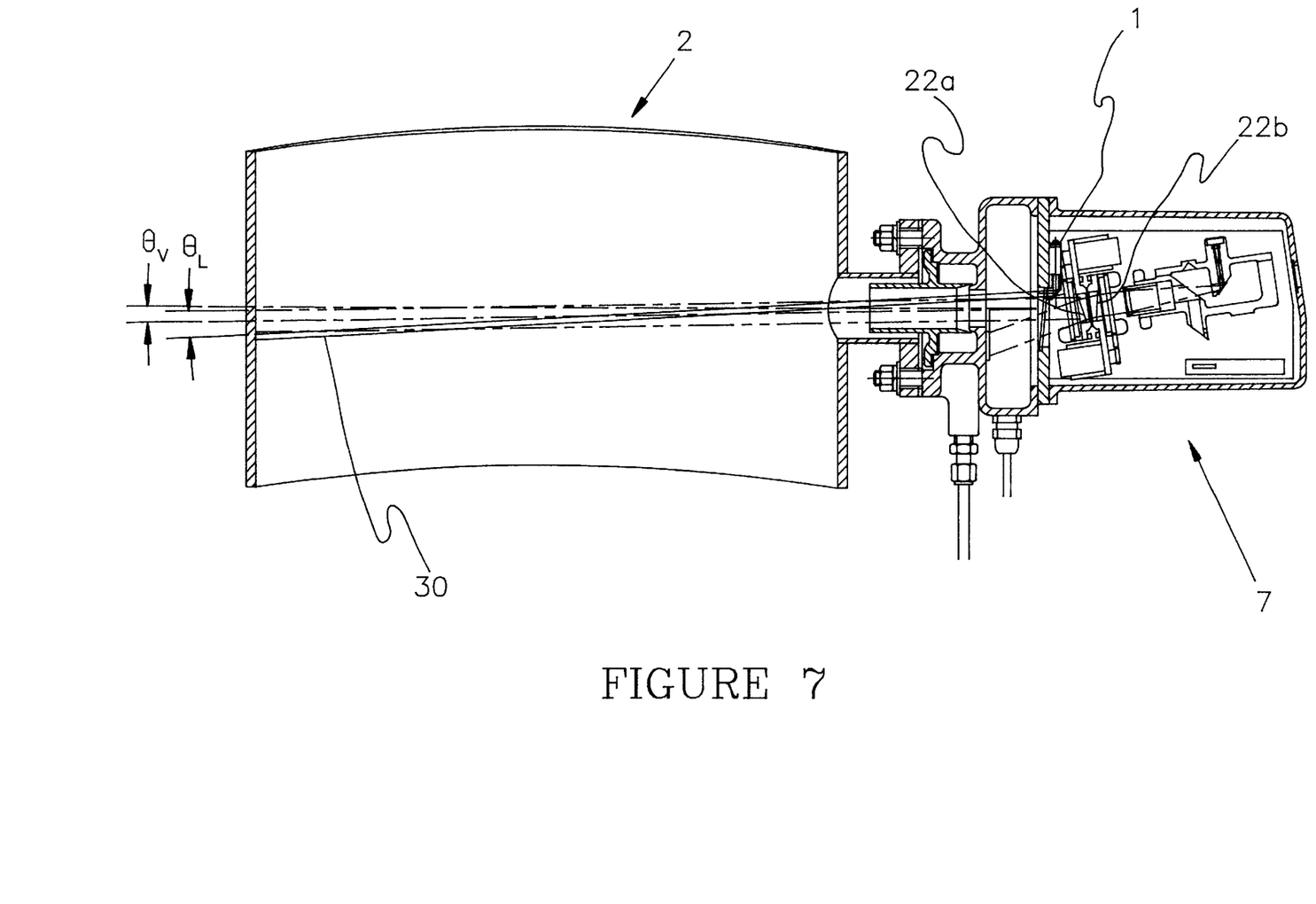
FIG. 7 is an optical diagram showing the light path when the viewing optics are steered low.

FIG. 1 shows the situation in which the prisms are aligned so as to cause the detector 32 to view scattered light from particles that are on the axis of symmetry of the system. This causes the system to view scattering at an intermittent distance in the stack corresponding to the overlap of the field of view 31 and the laser beam 30. FIG. 6 shows the situation in which the two prisms are aligned such as to elevate the field of view by an angle $\Phi_V$ with respect to the axis of symmetry of the system A—A. This will result in a shorter region of overlap between the field of view and the laser beam, effectively restricting the measurement to a volume near the side of conduit 2 on which main assembly 7 is mounted. FIG. 7 shows the situation in which the two prisms are aligned such as to lower the field of view by an angle $\Phi_V$ with respect to the axis of symmetry of the system A—A. This will result in a longer region of overlap between the field of view and the laser beam, for a longer measurement path encompassing most of conduit 2. The ability to thereby steer the field of view presents three immediate benefits. If, when conduit 2 is clear of any particulates, the beam is steered to a view angle $\Phi_V$ just slightly larger than the largest angle at which reflections from the far-side wall of conduit 2 are detected, the system will be automatically adjusted for the longest possible measurement path for the best integration of the signal. If the viewing angle is then reduced to that angle which provides the greatest signal to detector 32, the system will be calibrated for maximum possible sensitivity. Finally, by correcting the measured intensities at various viewing angles for geometrical effects, a spatial profile of the particulate distribution within conduit 2 can be calculated. This can be useful for analyzing particulate stratification within conduit 2.

Although we prefer to use two prisms to steer the beam, several other mechanisms could be used. We could provide a pair of mirrors and steer the beam via orthogonal movement of the pair of mirrors. A concave lens or combination of lenses could be used. In that embodiment linear movement of an orthogonally oriented two-dimensional concave lens will steer the beam.

As seen most clearly in FIG. 2, beam converger 11, mirror 36, field stop 35 and detector 32 are affixed to an optical bench 12 that preferably is a precision casting. The components, along with the view-steering apparatus 10, are affixed to a base-plate 9 mounted on a plate 8 which also contains the front window 38. Intermediate housing 51 provides access to a calibration target to be described later. Purge housing 52 includes provision for a purge port 53 connected to nozzle 3 which provides protection of the window 38 and calibration target 13 from heat and gases. Purge air is supplied through line 54 that preferably is connected to a source of dry, filtered, instrument air. The overall apparatus is designed so that the optical assembly 7 fits onto a standard industrial flange while contacting a seal 5. The beam steering assembly is preferably controlled by a microprocessor (not shown) positioned within the optical assembly. Power and communication lines (not shown) for the microprocessor, motors, encoders light source and detectors are provided through conduits 55. The entire assembly is protected from rain, dust and other factors by a cover 14. We prefer that the view steering optics 10 and the centerline of the optical bench 12 be tilted at an angle of 8.5° with respect to the axis of symmetry A—A because the optical nature of wedge prisms makes it possible to move the direction of view in independent orthogonal directions via independent movement of the prisms when in this orientation.

FIG. 3 is an inboard view of the intermediate housing 51. The calibration target as depicted shows in chain lines two alternate areas 104 and 107 which may be viewed via movement of the steering optics. One of the two locations is a flat black or other absorbing surface 104 which is not illuminated and which thereby serves to simulate the situation of zero particulate in the conduit and consequently no back-scattered light in the viewing optics. The second calibration target includes a standard photography disc 107 which is illuminated by a portion of the beam of the laser via a relay optics 6 mounted on the face of plate 8. The relay optics 6 are shown in FIG. 3 as a phantom figure. Relay optics 6 consist of a pair of mirrors 6a and 6b at the end of a barrel tube, which receive a representative portion of light from laser 10 via beam splitter 34 and translate that light beam so as to illuminate a portion 106 of calibration target 107 which, when viewed by the detector, presents to the detector an amount of energy approximately equal to the energy that would be scattered from particulate in the conduit under particulate concentrations typical to the specific application into which the system is installed. By adjusting the steering of the viewing optics to include more or less of the illuminated portion 106 of photography disc 107, relative to the non-illuminated portion of 107, the optical equivalency of the calibration target 107 and concentrations of particulates for any specific conduit 2 can be achieved with any desired degree of accuracy. This feature of our invention eliminates the need for mechanical adjustment of a calibration device when the full scale of the instrument is changed.

We prefer to provide electronic and microprocessor components and software programs in the electronic module 15, shown in FIG. 2, to provide automatic particulate profile, and to provide means for automatic checks of system calibration without the need of moving parts other than the beam-steering mechanism. Electronic module 15 includes a drive controller 16 which can be used to operate the laser 30 in a pulsed mode so as to reduce the fraction of time that the laser 30 is operating so as to extend laser life.

Although we have shown and described certain present preferred embodiments of our monitor and method for monitoring size, distribution and concentration of particulates in a conduit, it should be distinctly understood that our invention is not limited thereto but may be variously embodied within the scope of the following claims.

We claim:

1. A method for monitoring spatial distribution and concentration of particulates in a conduit which has a window that allows passage of at least one light beam through the window and across the conduit comprising:

a. positioning a solid state light source so that a light beam from the solid state light source is passed through the window and across the conduit along an optical axis at a selected angle $\Theta_L$ with respect to an axis of symmetry of the system;

b. positioning a detector with respect to a beam steering mechanism having beam steering optics and viewing optics such that the detector is illuminated by light scattered from particulates within the conduit where the beam steering optics cause the detector to receive only light scattered along an axis which forms a selectable viewing angle $\Theta_V$ with respect to the axis of symmetry of the system, said detector thereby producing a signal corresponding to intensity of light scattered in a direction of the viewing optics by particulates resident within a viewing volume defined by an intersection of the projected light beam and a view path of the beam steering optics, c. detecting light scattered from the light beam striking particulates within the viewing volume when the viewing optics is aimed at a known angle $\Theta^V$;

e. measuring an intensity of the detected scattered light;

g. using the intensity of detected scattered light to calculate concentration of particles in the conduit.

2. The method of claim 1 wherein the viewing angle $\Theta_V$ is changed so as to cause the detector to view scattered light from a different viewing volume within the conduit.

3. The method of claim 1 wherein the detector and beam steering optics are within a housing that also contains the solid state light source.

4. The method of claim 1 wherein the beam steering mechanism is comprised of a pair of rotatable wedge prisms.

5. The method of claim 4 also comprising using a first servo motor to rotate one wedge prism and a second servo motor to rotate the other wedge prism.

6. The method of claim 4 also comprising tracking positions of the first wedge prism with a first encoder connected to the first wedge prism and tracking positions of the second wedge prism with a second encoder connected to the second wedge prism.

7. The method of claim 1 also comprising:

a. providing a calibration assembly having at least one region that is optically absorbing and is not illuminated with any portion of light from the solid state light source, b. steering the viewing optics so as to view the at least one region so that the detector experiences an optical signal equivalent to that which would be experienced when viewing the stack in the absence of any particulates;

c. measuring an intensity of light gathered from the at least one region; and d. comparing that measurement with an expected intensity corresponding to the at least one region.

8. The method of claim 1 also comprising:

a. providing a calibration assembly having at least one region that is partially and diffusely reflective and is illuminated with a portion of light from the solid state light source;

b. steering the viewing optics so as to view the at least one region so that the detector experiences an optical signal equivalent to that which would be experienced when viewing the stack in the presence of a concentration of particles;

c. measuring an intensity of light gathered from the at least one region; and d. comparing that measurement with an expected intensity corresponding to the at least one region.

9. The method of claim 1 also comprising splitting a beam from the solid state light source into a reference beam and a measuring beam and directing the measuring beam through the stack and the reference beam to a reference region.

10. The method of claim 1 wherein the solid state light source is a laser.

11. A monitor comprised of:

a. a housing sized and configured for attachment to a conduit and having a window through which light may pass;

b. a solid state light source within the housing;

c. a beam steering unit within the housing positioned to direct a light beam from the light source through the window and across the conduit, the beam steering unit being capable of directing the light beam to one of any of a plurality of locations as selected by a user; and d. at least one detector positioned to receive light from the light beam which has been scattered after striking particles in the conduit which detector produces a signal corresponding to intensity of light received by the detector the signal being useful for measuring at least one of opacity of a medium passing through the conduit and light scattered by particulates in the conduit.

12. The monitor of claim 11 also comprising a beam splitter positioned within the housing for splitting a beam from the solid state light source into a reference beam and a measuring beam and directing the measuring beam through the conduit and the reference beam to a reference region.

13. A monitor comprised of:

a. a housing sized and configured for attachment to a conduit and having a window through which light may pass;

b. a solid state light source within the housing;

c. a beam steering unit comprised of a pair of rotatable wedge prisms in an optical path of the light beam such that independent motion of either prism will cause orthogonal movement of the light beam from the solid state light source.

14. The monitor of claim 13 wherein the beam steering unit also comprises a first servo motor connected to rotate one wedge prism and a second servo motor connected to rotate the other wedge prism.

15. The monitor of claim 14 wherein the beam steering unit also comprises a first encoder connected to the first wedge prism and a second encoder connected to the second wedge prism.

16. The monitor of claim 11 also comprising a calibration assembly having at least one region of a known reflectivity which assembly is positioned within the housing so that the beam steering unit may direct a light beam onto the at least one region for reflection to the detector.

17. The monitor of claim 11 wherein the solid state light source is a laser.

* * * * *